(12) United States Patent
Cheng et al.

(10) Patent No.: US 7,939,111 B2
(45) Date of Patent: May 10, 2011

(54) LINGONBERRY EXTRACT, METHODS OF PREPARING, AND USES THEREOF

(75) Inventors: Qiaojie Cheng, Beijing (CN); Yanmei Li, Beijing (CN); Xiarui Dou, Beijing (CN)

(73) Assignee: Beijing Gingko-Group Biological Technology Co., Ltd., Beijing (CN)

( * ) Notice: Subject to any disclaimer, the term of this patent is extended or adjusted under 35 U.S.C. 154(b) by 69 days.

(21) Appl. No.: 11/939,205

(22) Filed: Nov. 13, 2007

(65) Prior Publication Data
US 2009/0011056 A1    Jan. 8, 2009

(51) Int. Cl.
*A01N 65/00* (2009.01)
(52) U.S. Cl. ...................................................... 424/725
(58) Field of Classification Search .................. None
See application file for complete search history.

(56) References Cited

FOREIGN PATENT DOCUMENTS
WO             01/01798        1/2001
WO       WO 2006134583    *  12/2006

OTHER PUBLICATIONS

Guo et al., "Application of membrane separation technology in food industry of China," *Membrane Science and Technology*, 2003, 23(4):197-201 (English language abstract included).
Guo et al., *Overseas Medicine-Plant Amedica Fascicule*, 1996, 11:196-204 (English language abstract included).
Li et al., *Guangdong Pharmacy*, 1999, 9:4. (English language abstract included).
Xiao et al., (1994) *Traditional Chinese Medicinal Chemistry*, Shanghai Science and Technology Press, p. 265 (English language abstract included).
Yang et al., *Chinese Traditional Patent Medicine*, 1995, 17:4-5 (English language abstract included).
You et al., *Chinese Journal of Cardiovascular Medicine*, 2003, 8(6):383-385 (English language abstract included).
Zhang et al., "Vasodilation of procyanidins from grape seeds on isolated rabbit aorta," *Chinese Traditional and Herbal Drugs*, 2006, 37:87-89 (English language abstract included).

* cited by examiner

*Primary Examiner* — Michael V Meller
(74) *Attorney, Agent, or Firm* — Fish & Richardson P.C.

(57) ABSTRACT

A first extract of lingonberry (*Vaccinium vitis-idaea* L.) comprising 5-35 wt % of anthocyanin, 20-95 wt % of proanthocyanin, less than 5 wt % of resveratrol, and the balance of other components, a second extract containing 60-98 wt % of resveratrol, and a third extract composed any ratio of comprising of the first and the second extracts. Methods for preparing the first and second extracts, and use of the extracts in preparation of compositions for eliminating oxygen free radicals, anti-aging, weight loss, preventing cardiovascular disease, inhibiting thrombosis, and promoting beauty.

1 Claim, 3 Drawing Sheets

LINGONBERRY EXTRACT, METHODS OF PREPARING, AND USES THEREOF

CROSS-REFERENCE TO RELATED APPLICATIONS

This application claims priority from Chinese Application Serial No. 200710122746.X, filed Jul. 4, 2007.

TECHNICAL FIELD

This invention relates to lingonberry extracts, methods for preparing such extracts, and uses thereof.

BACKGROUND

Anthocyanin, also known as anthocyan, is a flavonoid compound, and has the following physiological activities: i) increasing flexibility of capillaries, thus improving the swellability and retractility of blood vessels and preventing angiorrhexis; ii) eliminating free radicals which may result in blood vessel sclerosis, thus preventing angiosclerosis; and iii) strengthening capillaries in eyes and other organs, and preventing pathological changes of these organs. Anthocyanins have been used in foods and medicines. Those used in foods typically have been anthocyanidins such as pelargonidin, cyanidin, delphinidin, peonidin, petunidin, malvidin, or anthocyanins formed by these anthocyanidins binding with glucose, galactose or arabinose respectively. Anthocyanins are mostly monosaccharides and diglycosides.

A proanthocyanin is a condensed tannin from a plant source, which produces anthocyanins when heated in an acidic medium. Proanthocyanins can reduce the levels of cholesterol and low-density lipoprotein, thus prevent thrombosis and cardio-cerebro-vascular disease, and protect DNA from damage of free radicals, thus preventing genetic mutations that may cause cancer.

Resveratrol and its glucoside are active polyphenol substances, and are abundantly contained in the Chinese medicine known as *Polygonurn cuspidaturn*. Apart from its strong antioxidant function, resveratrol can inhibit three major stages (induction, initiation and development) of cytometaplasia and tissue mutation in the process of cancer development. It has been reported that resveratrol can delay the aging process by protecting DNA from chemical damage. In addition, experiments with regard to the life-increasing mechanism of resveratrol revealed that resveratrol can increase life span by about 70% by activating Sir2 enzymatic expression. Hence, resveratrol can influence health by activating the Sir2 enzyme in different levels and paths.

SUMMARY

It is an object of this document to provide an exact enriched with anthocyanin, proanthocyanin, and resveratrol from lingonberry fruit.

Lingonberry (*Vaccinium vitis-idaea* L.), also known as red bean, is an evergreen dwarf shrub with a height of 15-30 cm, belongs to *Vaccinium* of Ericaceae, and is a perennial tree species of deciduous leaf or evergreen shrub or dwarf shrub. It has origins in alpine areas of northeast of China, Korea, the former Soviet Union, North America and Northern Europe, often living together with bog bilberry (*Vaccinium uliginosum* L.). Its leaves are evergreen and herbaceous. Lingonberry has excellent cold hardiness and resistance to drought. Lingonberry fruit is brilliant red, with an acerbic taste.

The inventors have found that lingonberry fruit is enriched in anthocyanin, proanthocyanin, and resveratrol. Accordingly, the present document provides methods for preparing extracts of lingonberry that can include the following steps:
  (a) extracting the fruit of lingonberry with a first solvent to obtain a first extract solution, wherein the first solvent is selected from the group consisting of alcohol, aqueous alcohol, water, aqueous acid, aqueous enzyme-containing solution, and aqueous acid-alcohol solution;
  (b) concentrating the first extracted solution to obtain a crude first extract;
  (c) purifying the crude first extract to obtain a first extract;
  (d) re-extracting with a second solvent the lingonberry fruit, which has been extracted by the first solvent, to obtain a second extract solution, wherein the second solvent is selected from ethyl acetate, benzene, toluene, chloroform, dichloromethane, n-hexane, acetone, methanol, ethanol, or a mixture thereof, or 70-95 wt % (percentage by weight) aqueous methanol or ethanol solution or aqueous solution containing 0.01-0.3 wt % cellulase or pectase;
  (e) concentrating the second extract solution to obtain a crude second extract; and
  (f) purifying the crude second extract to obtain a second extract of lingonberry in which the main component is resveratrol.

In one embodiment, in step (a), the first solvent is an aqueous acid solution or an aqueous acid-alcohol solution, and the extracting is performed at 20-50° C. Alternatively, the first solvent can be an aqueous alcohol solution and the extracting can be performed at a temperature of 40-90° C., or the first solvent can be an aqueous enzyme-containing solution and the enzymolysis can be performed at a temperature of 30-60° C.

In step (c), the crude first extract can be eluted with 30-95 wt % alcohol through a macroporous adsorption resin column or an ion exchange resin column, and the obtained alcohol solution can be concentrated and dried to obtain the first extract of lingonberry. Alternatively, purification can be performed by membrane filtration, including treating the crude first extract with an ultrafiltration membrane, followed by vacuum concentrating or filtering the obtained filtrate through a reverse osmosis (or nanofiltration) membrane, and drying to obtain the first extract of lingonberry. Alternatively, purification can be performed by combining the two methods described above, including filtering the crude first extract with an ultrafiltration membrane, purifying it on a resin column, and drying to obtain the first extract of lingonberry, or purifying the crude first extract on a resin column, filtering the filtrate with an ultrafiltration membrane, and drying to obtain the first extract of lingonberry.

In step (d), the re-extracting can be performed under light-proof and inert atmosphere to obtain the second extract solution. In step (f), the crude second extract obtained in the step (e) can be purified on silica gel column with n-hexane, ethyl acetate, acetone, chloroform, dichloromethane, methanol, ethanol or the mixture thereof to obtain the second extract of lingonberry.

This document also provides lingonberry extracts comprising 5-35 wt % (e.g., 5-20 wt %) of anthocyanin, 20-95 wt % (e.g., 50-95 wt %) of proanthocyanin, and less than 5 wt % (e.g., less than 2 wt %) of resveratrol, with the balance of the extract containing other components.

In another aspect, this document provides a lingonberry extract containing 60-98 wt % of resveratrol.

The products provided herein can be used, for example, in functional foods for anti-aging, weight loss, eliminating oxygen free radicals, preventing cardiovascular and cerebrovascular diseases, inhibiting thrombosis, and in beauty treatments.

Thus, in one aspect, this document features a process for preparing an extract of lingonberry (*Vaccinium vitis-idaea* L.), comprising the steps of: (a) extracting the fruit of lingonberry with a first solvent selected from the group consisting of alcohol, aqueous alcohol solution, water, aqueous acid solution, aqueous enzyme-containing solution, and aqueous acid-alcohol solution, and then isolating to obtain a first extract solution; (b) evaporating the first extract solution to obtain a crude first extract; and (c) purifying the crude first extract to obtain a first extract product. In step (a), the first solvent can be an aqueous acid solution or an aqueous acid-alcohol solution containing no more than 10 wt % of hydrochloric acid, sulfuric acid, acetic acid or citric acid, or an aqueous solution containing 0.05-0.2 wt % of cellulase or pectinase. In step (a), the first solvent can be an aqueous acid solution or an aqueous acid-alcohol solution, and the extraction is performed at a temperature of 20-50° C.; or the first solvent can be an aqueous alcohol solution, and the extraction is performed at a temperature of 40-90° C.; or the first solvent can be an aqueous enzyme-containing solution, and the extraction is performed at a temperature of 30-60° C. Step (c) can comprise purifying the crude first extract with an absorptive resin or an ion exchange resin, including transferring the crude first extract into an absorptive resin column or an ion exchange resin column, eluting with 30-95% ethanol, concentrating the obtained ethanol solution and drying to obtain a first extract of lingonberry; or purifying the crude first extract with an ultra-filtration membrane, including passing the crude first extract through an ultrafiltration membrane, concentrating the obtained retentate or passing it by a reverse osmosis membrane, and drying the obtained concentrated solution to obtain the first extract of lingonberry; or combining the above two methods, including passing the crude first extract through an ultrafiltration membrane, purifying the obtained retentate with a resin column, and drying to obtain the first extract of lingonberry; or purifying the crude first extract with a resin column, then treating with an ultrafiltration membrane, and drying to obtain the first extract of lingonberry.

The process can further comprise: (d) re-extracting the fruit of lingonberry, which has been extracted by the first solvent, with a second solvent to obtain a second extract solution, wherein the second solvent is selected the group consisting of ethyl acetate, benzene, toluene, chloroform, dichloromethane, n-hexane, acetone, methanol, ethanol, or a mixture thereof, or methanol or 70-95% ethanol aqueous solution, or an enzyme aqueous solution containing 0.01-0.3 wt % of cellulase or pectase; (e) concentrating the second extract solution to obtain a crude second extract; and (f) purifying the crude second extract to obtain a second extract of lingonberry in which the main component is resveratrol. In step (f), the purification can be performed using silica gel column chromatography with n-hexane, ethyl acetate, acetone, chloroform, dichlormethane, methanol, ethanol or a mixture solvent thereof as the eluant to obtain the second extract of lingonberry from the crude second extract. Step (d) can be performed one or two times under a light-proof and inert atmosphere to obtain the second extract solution.

In another aspect, this document features a process for preparing an extract of lingonberry, comprising: (a) extracting the fruit of lingonberry with a first solvent selected from the group consisting of alcohol, aqueous alcohol solution, water, aqueous acid solution, aqueous enzyme-containing solution, and aqueous acid-alcohol solution, and then isolating to obtain a first extract solution; (b) concentrating the first extract solution to obtain a crude first extract; (c) purifying the crude first extract to obtain a first extract; (d) re-extracting the fruit of lingonberry, which has extracted with the first solvent, with a second solvent to obtain a second extract solution, wherein the second extract solution is selected from ethyl acetate, benzene, toluene, chloroform, dichloromethane, n-hexane, acetone, methanol, ethanol, and a mixture thereof, or 60-95 wt % methanol or ethanol aqueous solution, or aqueous enzyme-containing solution containing 0.01-0.3 wt % of cellulase or pectase; (e) concentrating the second extract solution to obtain a crude second extract; and (f) purifying the crude second extract to obtain a second extract of lingonberry in which the main component is resveratrol. In step (a), the first solvent can be an aqueous acid solution or an aqueous acid-alcohol solution, and the extraction can be performed at 20-50° C.; or the first solvent can be an aqueous alcohol solution, and the extraction can be performed at 40-90° C.; or the first solvent can be an enzyme aqueous solution, and the enzymolysis can be performed at 30-60° C.; and the process can comprise: in step (b), concentrating the first extract solution to obtain the crude first extract; in step (c), transferring the crude first extract into an absorptive resin column or an ion exchange resin column, eluting with 30-95% ethanol, concentrating the obtained ethanol solution, and drying to obtain a first extract of lingonberry; or purifying the crude first extract by an ultra-filtration membrane, including passing the crude first extract through an ultrafiltration membrane, concentrating the obtained retentate or passing it by a reverse osmosis membrane, and drying the obtained concentrated solution to obtain the first extract of lingonberry; or performing the purification by combining the above two methods, including passing the crude first extract through an ultrafiltration membrane, purifying the obtained retentate with a resin column, and drying to obtain the first extract of lingonberry; or purifying the crude first extract by a resin column, then treating with an ultrafiltration membrane, and drying to obtain the first extract of lingonberry; in step (d), performing the re-extracting under a light-proof and inert atmosphere to obtain the second extract solution; in step (e), concentrating the second extract solution to obtain the crude second extract; and in step (f), purifying the crude second extract by silica gel column chromatography with n-hexane, ethyl acetate, acetone, chloroform, dichlormethane, methanol, ethanol, or a mixture thereof to obtain the second extract of lingonberry.

In another aspect, this document features an extract of lingonberry comprised of 5-35 wt % of anthocyanin, 20-95 wt % of proanthocyanin, less than 5 wt % of resveratrol, and the balance of other components. The extract can be comprised of 5-20 wt % of anthocyanin, 50-95 wt % of proanthocyanin, less than 2 wt % of resveratrol, and the balance of other components. The anthocyanin can substantively comprise cyanidin-3-galactose, cyanidin-3-glucose and cyanidin-3-arabinose.

In another aspect, this document features an extract of lingonberry, comprising 60-98 wt % of resveratrol.

This document also features a composition comprising: an extract of lingonberry comprised of 5-20 wt % of anthocyanin, 50-95 wt % of proanthocyanin, less than 2 wt % of resveratrol, and the balance of other components, and an extract of lingonberry comprising 60-98 wt % of resveratrol.

In still another aspect, this document features a method for reducing the amount of oxygen free radicals in a cell, comprising contacting the cell with an extract of lingonberry, wherein the extract is (a) a lingonberry extract comprised of 5-20 wt % of anthocyanin, 50-95 wt % of proanthocyanin, less than 2 wt % of resveratrol, and the balance of other components, (b) an extract of lingonberry comprising 60-98 wt % of resveratrol, or (c) a combination of (a) and (b).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

The term "anthocyanin" refers to a chromene derivative that gives the flower, fruit, leaf, stem, etc. of plants a color such as blue, purple, or red. Most of these derivatives can condense with glucose, galactose, or rhamnose, or some pentoses, to form anthocyanin. Examples of anthocyanins include pelargonidin, cyanidin, delphinidin, peonidin, petunnidin, malvidin, hireutidin and gesnerin.

The term "proanthocyanin" refers to a category of polyphenol compounds that exist in plants and result in anthocyanin when heated in acidic mediums.

The term "other components" refers to edible substances that are extracted together with the expected components under extraction conditions as described herein.

In one aspect, this document provides extracts of lingonberry that are substantially comprised of anthocyanin, proanthocyanin, and resveratrol. In some embodiments, an extract can be comprised of 5-35 wt % of anthocyanin, 20-95 wt % of proanthocyanin, and less than 5 wt % of resveratrol, with the balance comprising other components. For example, an extract of lingonberry obtained according to a method as described herein can contain 5-20 wt % of anthocyanin, 50-95 wt % of proanthocyanin, and less than 2 wt % of resveratrol, with the balance being of other components. The anthocyanin can mainly include cyanidin-3-galactose, cyanidin-3-glucose, and cyanidin-3-arabinose, and the proanthocyanin can mainly include proanthocyanin B1, proanthocyanin B2, and proanthocyanin C1.

In a second aspect, also provided herein are extracts of lingonberry that contain 60-98 wt % of resveratrol. In some embodiments, for example, an extract of lingonberry can contain 75-85 wt % of resveratrol (e.g., 80 wt % of resveratrol).

In a third aspect, this document provides compositions of lingonberry extracts, comprised of, at any weight ratio, the first and second extracts of lingonberry described above.

In a fourth aspect, this document provides methods for preparing the above-described extracts of lingonberry.

Anthocyanin and proanthocyanin are polyhydroxy flavones. Any suitable extraction method, including those known in the art, can be used to extract polyhydroxy flavones in the methods provided herein. The methods typically include extraction and purification steps. As used herein, "extraction" refers to a process for abstracting objective components from raw material of lingonberry by means of physical and/or chemical methods. "Isolation/isolating" and "purification/purifying" refer to isolating objective components from a crude extract, typically through physical methods. The extraction method can be, for example, solvent extraction, ultrasonic extraction, enzymatic extraction, or supercritical fluid extraction. Solvent extraction and enzymatic extraction methods can be particularly useful.

Any suitable method(s) can be used to isolate anthocyanin and proanthocyanin from a crude first extract. These methods include, for example, those frequently used in the art for isolating flavone compounds, such as solvent extraction, alkali-extraction and acid-precipitation, polyamide column chromatography, silica gel column chromatography, boracic acid complexation, pH gradient extraction, and gel column chromatography. Such methods have been described in, for example, Xiao et al. (1994) *Traditional Chinese Medicinal Chemistry*, Shanghai Science and Technology Press, p. 265; and Li et al. (1999) *Guangdong Pharmacy* 9:4. Membrane filtration and adsorption resin methods can be particularly useful.

In some embodiments, lingonberry extraction can be performed using a first solvent such as an alcohol, an aqueous alcohol solution, water, an aqueous acid solution, or an aqueous acid-alcohol solution, and the extraction method can be any of the following.

1) Water extraction: Hot water extraction can be used to extract various flavonoid glycosides. During this type of procedure, a raw material is placed into hot or even boiling water to damage enzymatic activity. The water amount, soaking time, extraction time, and number of repetitions can be varied. Typically, it is feasible to use 1-5 fold of water (e.g., 1-3 fold of water), which can be heated to 30-100° C. (e.g., 30-80° C., 30-60° C., or 40-50° C.). The extraction time can be varied according to the temperature. For example, extraction time can be shorter at a higher temperature and longer at a lower temperature. In view of production efficiency, the extraction time typically is 24 hours or less (e.g., 16 hours or less, 8 hours or less, 4 hours or less, or 1 to 2 hours). Additionally, the above extraction process can be repeated several times. Generally, extraction time, temperature and repetitions can be considered interactively. For example, extraction may be done fewer times or even once at a higher temperature or for a longer extraction time. In some embodiments, the extraction can be repeated twice with 3-5 fold water at 60-80° C. for 16 hours. A small amount of inorganic acid or organic acid can be added to the water, wherein the term "small amount" refers to an amount of acid that is no more than 10% by weight (e.g., no more than 5% by weight, or no more than 3% by weight). The amount of acid, however, typically is enough to adjust the pH of aqueous solution to no more than 3 (e.g., 3, 2, or 1). Any suitable acid can be used, and hydrochloric acid and sulfuric acid which have lower cost can be particularly useful. Other suitable acids include acetic acid, oxalic acid, malonic acid, butanedioic acid, and citric acid. When acid is used, extraction can be performed at ambient temperature (20° C.). In some embodiments, extraction can be performed 1-2 times in 3-5 fold water, at a pH in the range of 1 to 2, at 40-50° C. for 60-90 minutes.

2) Ethanol or methanol extraction: Ethanol or methanol is the most common extractant for flavone compounds. A high concentration of aqueous alcohol solution (e.g., 90-95 wt %) can be suitable for extracting aglycones, and alcohol at about 60 wt % can be suitable for extracting glycosides. Typically, an aqueous alcohol solution with an alcohol content in the range of 30-70 wt % is suitable. The extraction time can be varied according to the temperature. For example, extraction time can be reduced at a higher temperature and longer at a lower temperature. For efficiency, the extraction time usually is 16 hours or less (e.g., 10 hours or less, 6 hours or less, or 1 or 2 hours). Additionally, the above extraction process may be repeated several times, e.g., 2-4 times. Generally, the extraction time, temperature and repetitions can be considered interactively. For example, extraction can be done fewer times or even once at a higher temperature or for a longer extraction time. In some embodiments, the extraction can be performed twice in 3-5 fold methanol aqueous solution, at 60-70° C. for 90 minutes each time.

3) Enzymatic methods: Enzymatic methods also can be used for extracting anthocyanin and proanthocyanin components. Examples of enzymes that can be used include glucose oxidase and cellulase. See, e.g., Li et al. (supra); Yang et al. (1995) *Chinese Traditional Patent Medicine*) 17:4; and Xu et al. (2001) *Chinese Traditional Patent Medicine* 32:37, which are incorporated herein by reference. As described in the examples below, enzymolysis conditions can include an aqueous solvent containing 0.05-0.2 wt % of cellulase or pectinase, a temperature of 30-60° C., and an ethanol concentration of 60%.

4) Membrane filtration: Extraction of anthocyanin and proanthocyanin also can be performed by membrane filtration methods. Such methods can include, for example, isolating the fruit extract of lingonberry by ceramic membrane separation, passing the permeate through an ultrafiltration membrane filter and then isolating the dialysate using a reverse osmosis membrane or a nanofiltration membrane. Examples of isolating flavone and polyphenol compounds using membrane filtration method are described, for example, in Guo et al. (2003) *Membrane Science and Technology* 23:197. In addition, WO/011001798 discloses a method for extracting anthocyanin from polyphenol-rich substances using membrane-filtration.

After extraction with a first solvent, the extracts can be re-extracted with a second solvent. Generally, the polarity of the second solvent is lower than that of the first solvent. Suitable second solvents can be selected from, for example, ethyl acetate, benzene, toluene, chloroform, dichloromethane, n-hexane, acetone, methanol, ethanol, or mixtures thereof, and 70-95 wt % aqueous methanol or ethanol solutions.

In some embodiments, ethyl acetate can be used. In other embodiments, 70-95 wt % ethanol aqueous solution or n-hexane can be used. Under the latter condition, the yield of the products may be reduced, but the content of resveratrol in the extract typically is higher.

In practice, lingonberry fruit can be extracted using a first solvent to separate out the first extracts of lingonberry, and then using a second solvent to re-extract the raw material that was extracted by the first solvent, to obtain a second extract solution. The extraction order also can be reversed, although the first order can be particularly useful.

Purification follows the extraction. Extract purification can be performed using, for example, a macroporous adsorption resin or ion exchange resin column chromatography, silica gel column chromatography, ultrafiltration, or a combination of the above methods. Macroporous resins that can be used include, without limitation, HP-20, ADS-F8, HPD-500, YWD-06, SP850, HP-30, S-861, D-101, DA-20 1, GDX-105, MD05271, CAD-40, XAD-4, and XAD-6. Ion exchange resins that can be used include, without limitation, CHPA-20, WK1, CKOSS, SP-550C, DEAE-650s, and SP-SPW.

Silica gel column chromatography can be used, for example, to purify a second extract of lingonberry as described herein (i.e., an extract containing 60-98 wt % of resveratrol). The elution solvent can be selected according to the properties of resveratrol. The solution used can be, for example, n-hexane, ethyl acetate, acetone, chloroform, dichloromethane, methanol, ethanol, or a mixture thereof.

A drying step, e.g., a vacuum drying step, typically is necessary after the purification step.

In some embodiments, lingonberry raw material can be extracted with a first solvent and the first extract solution can be filtered out, the solid residue can be extracted with the second solvent and the second extract solution filtered out, and then the first extract solution and the second extract solution can be treated to obtain a first extract and a second extract of lingonberry, respectively. These extracts can be combined to prepare lingonberry compositions. In some embodiments, therefore, methods for preparing the above extracts of lingonberry can include the following steps:

(a) extraction: extracting lingonberry raw material with a first solvent to obtain a first extract solution of lingonberry;

(b) purification: purifying the first extract solution obtained in step (a);

(c) drying: drying the purified substance obtained in step (b) to obtain a first extract of lingonberry;

(d) extraction: re-extracting the raw material, which was extracted with the first solvent, with the second solvent to obtain a second extract solution of lingonberry;

(e) purification: purifying the second extract solution to obtain a second extract of lingonberry (typically having a high content of resveratrol); and (f) mixing the first extract and the second extract at any ratio to obtain an extract composition of lingonberry.

In step (f), the ratio of first extract and second extract can be designed according to the application of an objective product. For example, a composition for use as an antioxidant may contain more of the first extract or even contain none of the second extract. A composition for use in anti-aging may contain the first extract dominantly and a smaller proportion of the second extract (e.g., the ratio of first extract:second extract may be about 10:1, about 12:1, about 15:1, about 7.5:1, or about 5:1). A composition for weight loss may contain the first extract and the second extract at substantially the same quantity (e.g., about 1:1, about 1.5:1, or about 1:1.5).

In some embodiments, a method can include the following steps:

(a) extraction: extracting lingonberry fruit with a hot aqueous acid solution, or an aqueous alcohol solution or an aqueous enzyme-containing solution, and then filtering to obtain a first extract solution;

(b) purification: purifying the first extract solution with a resin or an ultrafiltration membrane;

(c) drying: drying the purified substance obtained in step (b) to obtain a first extract of lingonberry;

(d) extraction: extracting the filtered residue, which has been extracted with acid aqueous solvent (or aqueous alcohol solution or enzyme aqueous solution), with a second solvent to obtain a second extract solution;

(e) purification: purifying the second extract solution to obtain a second extract of lingonberry (typically having a high content of resveratrol); and
(f) mixing the first extract and the second extract at the ratio of 0.001:100 to 100:0.001 to obtain a third extract of lingonberry.

In more particular embodiments, a method for preparing the above extracts of lingonberry can contain following steps:
(a) extraction: extracting lingonberry fruit with a hydrochloric acid, sulfuric acid, or aqueous acetic acid solution of 1-5 wt %; methanol or ethanol aqueous solution (e.g., 30-70 wt %); or an aqueous solution of cellulase or pectinase (e.g., 0.05-0.2 wt %), and filtering under a reduced pressure to obtain a first extract solution;
(b) purification: (i) concentrating to substantially remove the solvent, transferring the concentrated solution onto a macroporous adsorption resin or an ion exchange resin column and, after washing to neutrality, eluting with 30-95 wt % ethanol; (ii) performing a purifying treatment using an ultrafiltration membrane; (iii) performing the purification by combining the above two methods, including filtering the crude first extract though an ultrafiltration membrane, purifying the retentate with a resin column, and drying to obtain the first extract of lingonberry, or (iv) alternatively, purifying the crude first extract with a resin column, filtering the eluate with an ultrafiltration membrane filter, and drying to obtain the first extract of lingonberry;
(c) drying: vacuum concentrating the ethanol solution obtained in step (b) and drying to obtain the first extract of lingonberry;
(d) extraction: extracting the residue that was filtered in step (a) with ethyl acetate, n-hexane, acetone, methanol, ethanol, or an aqueous solution thereof to obtain a second extract solution (this step may be performed 1-2 times under a light-proof and inert atmosphere);
(e) purification: purifying the second extract solution obtained in step (d) by silica gel column chromatography with a solvent selected from n-hexane, ethyl acetate, acetone, methanol, ethanol, or a mixture thereof in order to obtain a second extract of lingonberry (typically having a high content of resveratrol); and
(f) mixing the first extract and the second extract at the ratio of 0.001:100 to 100:0.001 to obtain the third extract of lingonberry.

Analysis

Analysis of a first extract and a second extract of lingonberry and compositions containing a combination thereof can be performed using, for example, high performance liquid chromatography (HPLC). For a first extract, the chromatographic conditions (Condition 1) can be:
chromatographic column: ODS-C18
gradient mobile phase: phase A, water: formic acid=90:10
phase B, water:acetonitrile:methanol=45:22.5:22.5
wave length: 540 nm
Alternatively, Condition 2 can be used:
chromatographic column: ODS-C18
gradient mobile phase: phase A, acetonitrile
phase B, phosphoric acid:water=67:31
wave length: 280 nm
For a second extract, the chromatographic conditions (Condition 3) can be:
chromatographic column: ODS-C18
gradient mobile phase: phase A, acetonitrile
phase B, water:formic acid=270:1
wave length: 303 nm Quantitative analyses of anthocyanin and resveratrol also can be performed using HPLC. For analysis of proanthocyanin, a potassium sodium tartrate method suitable for polyphenols of grape seed can be used—i.e., using the specific reaction of polyphenol with tartaric acid iron in a phosphate buffer solution at pH=7.5, and then quantitating the reaction product at a maximum absorption wavelength 540 nm to obtain the sum of the polyphenols, and subtracting the amount of anthocyanin determined by HPLC from the sum to obtain the amount of proanthocyanin.

Applications

The main pigment components in extracts of lingonberry are anthocyanin and proanthocyanin, wherein anthocyanin is essentially cyanidin-3-galactoside. Anthocyanin is an antioxidant. Proanthocyanin can be decomposed into anthocyanin in aqueous acid solution with heating, and can efficiently reduce the level of cholesterol and low density lipoprotein, prevent thrombosis and cardiovascular and cerebrovascular disease, and protect cellular DNA from damage caused by free radicals, thus preventing genetic mutations that may cause cancer.

Extracts of lingonberry also contain resveratrol and resveratrol glucoside. Resveratrol (glucoside) is an active polyphenol. In addition to their function as antioxidants, polyphenols may be useful for treating cancer and inhibiting tumorigenesis, because of their ability to inhibit three major stages (induction, initiation and development) of cytometaplasia and tissue mutation. Resveratrol also may delay the aging process by protecting chromosomal DNA from chemical damage. In addition, resveratrol has been shown to prolong the life span of yeast by about 70% by activating Sir2 enzymatic expression. Thus, resveratrol can influence health via multiple pathways.

The scope of this document thus also includes the use of lingonberry extracts for anti-aging, reducing weight, beauty treatment, and treating cardiovascular and cerebrovascular disease.

In studies using the orthophenanthroline $Fe^{2+}$ oxidation method, the inventors have found that lingonberry extract can remove hydroxy radicals, and its potency is positively correlated with its concentration. The $IC_{50}$ for lingonberry extract was much less than that of ascorbic acid (Vc) under the same experimental conditions (described in the Examples below). It thus can be concluded that lingonberry extract has a greater scavenging capability than ascorbic acid, and it has significant anti-oxidation effects in vitro.

Free radicals play an important role in aging and various diseases. Thus, due to their antioxidation abilities, extracts of lingonberry obtained according to the methods provided herein may have be useful in compositions for anti-aging, weight loss, and tooth whitening, as well as in anti-wrinkle formulations and for treating cardiovascular disease.

Free radicals are generated continuously in the process of cellular metabolism. Other external stimulating factors, such as ultra-violet rays and chemical substances, also can facilitate generation of free radicals. The excessive accumulation of these free radicals can damage biomacromolecular substances, such as DNA and proteins, thereby leading to aging of organisms. Anti-oxidation substances such as anthocyanin, proanthocyanin and resveratrol, which are abundantly contained in lingonberry extracts, can efficiently remove free radicals and further play an important role in anti-aging. The inventors have conducted experiments (described below) showing that aged mice fed lingonberry extract exhibited substantially lower levels of MDA, a degradation product of lipid peroxide in blood, and a higher activity of glutathione peroxidase (GSH-Px) in blood serum. It can be concluded that the lingonberry extract can act against aging through its antioxidation effects.

Upon treating nutritional obese rats (resulting from a high-lipid diet) with extracts of lingonberry as provided herein, the inventors found that the rats showed a slower increase in body weight, whereas their diet consumption were not influenced. In addition, it was found that the fat around their testes and kidneys was remarkably decreased. Thus, extracts of lingonberry can inhibit fat accumulation in body while having no obvious appetite inhibition. Therefore, the extract can be used as a healthy diet food.

Proanthocyanin can inhibit platelet aggregation by inhibiting thromboxane TXA2 (see, Guo et al. (1996) *Overseas Medicine-Plant Amedica Fascicule* 11:196-204) that Experiments also have demonstrated that grape seed proanthocyanins can remarkably inhibit oxidation of low density lipoprotein in blood plasma due to their anti-oxidative properties, and have significance in preventing and treating atherosclerosis, although they cannot influence blood fat level in rabbits suffering from experimental hyperlipidemia (You et al. (2003) *Chinese Journal of Cardiovascular Medicine* 8:383-385). Research has shown that proanthocyanins in grape seed can have a relaxation effect on ex vivo aortic annuli of rabbits, and the effect is relative to their facilitation to NO release of endotheliocytes (Zhang et al. (2006) *Chinese Traditional and Herbal Drugs* 37:87-89). Lingonberry extracts as provided in the first aspect described herein are rich in anthocyanin and proanthocyanin and contain a small amount of resveratrol, and therefore may be useful for inhibiting thrombosis, reducing blood fat, and relaxing blood vessels, and can be used for preventing and treating high blood pressure, atherosclerosis, thrombosis disease, etc.

In addition, lingonberry extracts can be used as beauty improvement products due to their anti-oxidation activities. Skin is a connective tissue, and collagen protein and elastin play important roles in skin texture. Moderate cross-linking of collagen can maintain skin integrity. Free radical oxidation in vivo, however, can result in over-cross-linking, which appears as wrinkles and vesicles on the skin. Anthocyanin and proanthocyanin can promote moderate cross-linking between collagen proteins by removing free radicals, thus keeping skin pliant, smooth, and elastic. On the other hand, free radicals or elastase can degrade elastin, while anthocyanin and proanthocyanin can reduce the amount of (e.g., eliminate) free radicals, and block generation of elastase, thereby improving skin health. Using a mouse skin photo-aging model constructed by exposing mice to ultra-violet rays (described below), the inventors found that the content of hydroxyproline and SOD activity in the skin of mice that had been fed lingonberry extracts were remarkably higher than in control animals. Consequently, lingonberry extracts, due to their anti-oxidation properties, can protect collagen in skin, thereby exerting anti-wrinkle properties.

The invention will be further described in the following examples, which do not limit the scope of the invention described in the claims.

EXAMPLES

Example 1

Preparation of a First Extract of Lingonberry 1000 g of lingonberry fruit was extracted with a hydrochloric acid solution (pH 1). The extract solution was transferred onto a resin column (HP20 macroporous adsorption resin) and eluted with 95% aqueous ethanol. The eluant was collected, vacuum concentrated at 50° C., and then spray dried to obtain about 8 g of the first extract of lingonberry.

The extract obtained contained 36.8% of anthocyanin, 52.7% of proanthocyanin, and 3.2% of resveratrol.

Example 2

Preparation of a First Extract of Lingonberry 1000 g of lingonberry fruit was extracted with an 80% ethanol aqueous solution. The extract solution obtained was transferred onto a resin column (CHPA20 ion exchange resin) and eluted with 60% aqueous ethanol. The eluant was collected, vacuum concentrated, and then spray dried to obtain about 9.5 g of the first extract of lingonberry.

The extract contained 19.6% of anthocyanin, 72.0% of proanthocyanin, and 1.4% of resveratrol.

Example 3

Preparation of a First Extract of Lingonberry 1000 g of lingonberry fruit was extracted with a 60% ethanol aqueous solution at 60° C. for 90 minutes. The extract solution was concentrated to remove ethanol. After dilution with water, the residue was transferred to a resin column (HP20 macroporous adsorption resin), and eluted with 95% ethanol. The eluant was collected, vacuum concentrated, and then spray dried to obtain about 8.1 g of the first extract of lingonberry.

The extract contained 24.5% of anthocyanin, 67.7% of proanthocyanin, and 1.5% of resveratrol.

Example 4

Preparation of a First Extract of Lingonberry 1000 g of lingonberry raw material was extracted using a 30% ethanol aqueous solution (pH 3). The extract solution was transferred onto a resin column (HP20 macroporous adsorption resin) and eluted with 95% ethanol. The eluant was collected, concentrated, and then spray dried to obtain about 7.6 g of the first extract of lingonberry.

The extract contained 27.8% of anthocyanin, 68.9% of proanthocyanin, and 0.7% of resveratrol.

Example 5

Preparation of a First Extract of Lingonberry 1000 g of lingonberry raw material was extracted using a 3-fold amount of 0.08% pectinase water solution. The mixture was incubated at 40° C. for 2 hours, and filtered to obtain an extract solution. The extract solution was treated with a macroporous adsorption resin to obtain about 6.3 g of the first extract of lingonberry.

The extract contained 34.8% of anthocyanin, 53.9% of proanthocyanin, and 1.2% of resveratrol.

Example 6

Preparation of a First Extract of Lingonberry 1000 g of lingonberry fruit was extracted using a 3-fold amount of 0.1% pectinase water solution. The mixture was incubated at about 40° C. for 2 hours, and then filtered to obtain an extract solution. The extract solution was filtered through an ultrafiltration membrane filter (molecular weight cut-off range of 2000). The retentate was purified using a CHPA20 ion exchange resin, eluted with 30% ethanol, concentrated, and spray dried to obtain about 8.5 g of the first extract of lingonberry.

The extract contained 5.2% of anthocyanin, 94.0% of proanthocyanin, and 0.5% of resveratrol.

Example 7

Preparation of a First Extract of Lingonberry 1000 g of lingonberry raw material was soaked in and extracted with a 3-fold amount of pure water, and the extract solution was filtered through a ceramic membrane filter (molecular weight cut-off range of 150,000). The obtained permeate was further filtered through an ultrafiltration membrane filter (molecular weight cut-off range of 2000), and the retentate was concentrated using a reverse osmosis membrane filter or was spray-dried directly to obtain about 15.9 g of the first extract of lingonberry.

Figure 1:
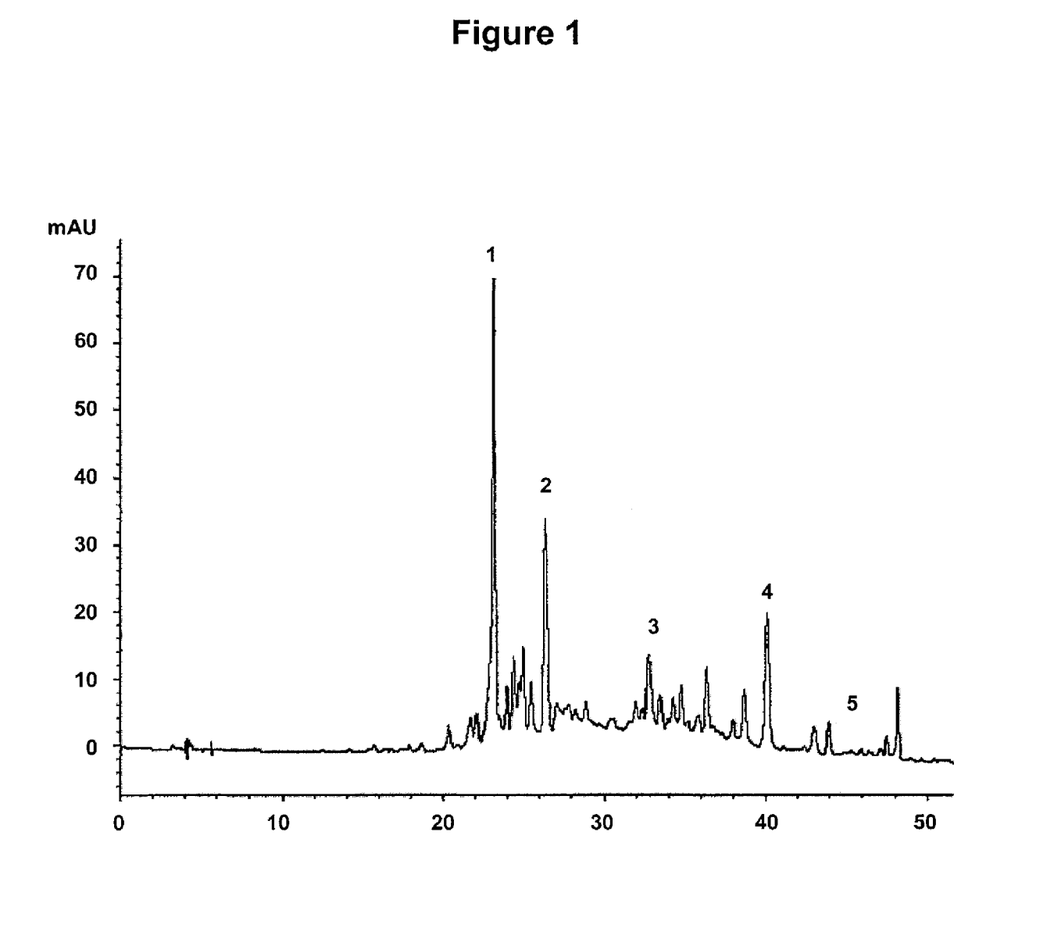
FIG. 1 is a HPLC spectrum of a first extract obtained using methods as provided herein. Peak 1=anthocyan, peaks 2-4=procyanidin, and peak 5=resveratrol.

The extract contained 5.2% of anthocyanin, 22.3% of proanthocyanin, and 0.5% of resveratrol. FIG. 1 shows the HPLC spectrum of the first extract in this example, using chromatographic Condition 1 as described above.

Example 8

Preparation of a Second Extract of Lingonberry

Fruit raw material (200 g), which had been extracted as described in Example 2, was further extracted with ethyl acetate under a light-proof and nitrogen gas atmosphere to obtain 9.8 g of yellowish paste. The paste was transferred onto a silica gel column, washed with n-hexane to remove impurities, and then gradiently eluted with a mixture of n-hexane and ethyl acetate. This procedure was monitored by TLC analysis. The resveratrol-rich fraction was collected to obtain a resveratrol crude product containing 80 wt % of resveratrol. The crude product was recrystallizated with ethanol to obtain 1.8 g of resveratrol crystal, the second extract of lingonberry containing 98% of resveratrol.

Example 9

Preparation of a Second Extract of Lingonberry

Figure 2:
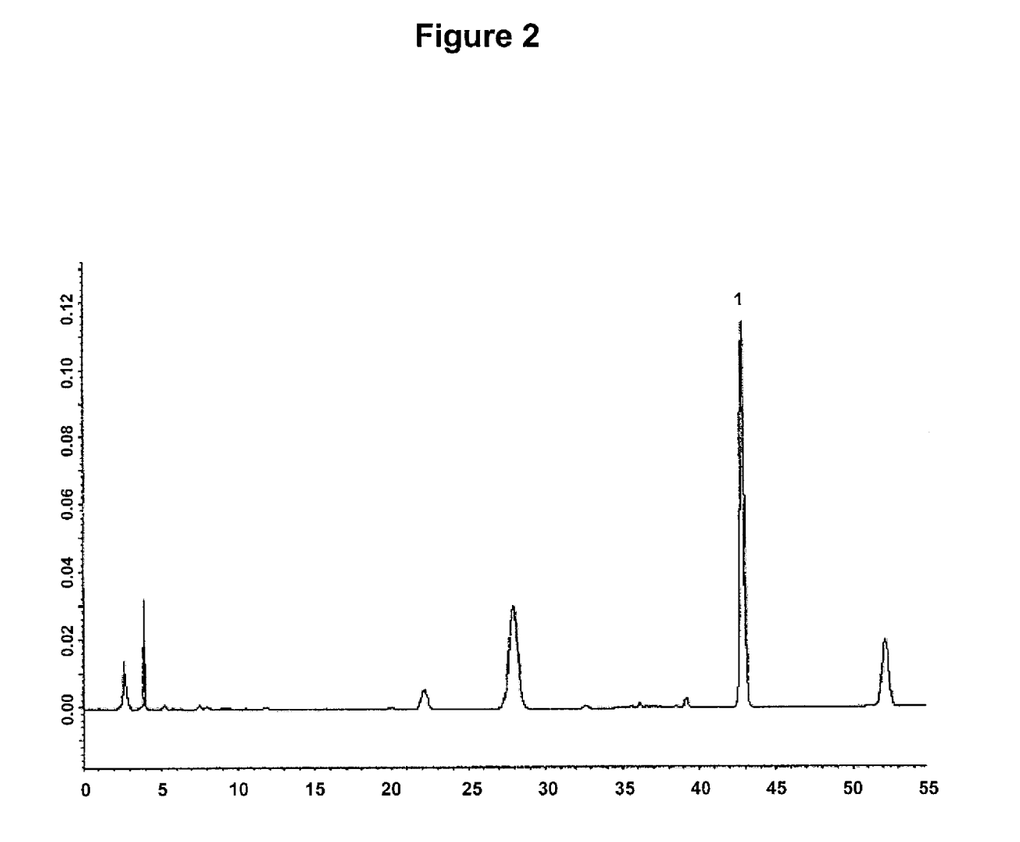
FIG. 2 is a HPLC spectrum of a second extract obtained as provided herein. Peak 1=resveratrol.

Fruit raw material (200 g), which had been extracted as described in Example 2, was further extracted with 800 ml 95% ethanol under a light-proof and nitrogen gas atmosphere to obtain a light yellow paste. The paste was transferred into a silica gel column, washed with n-hexane to remove impurities, and then gradiently eluted with a mixture of n-hexane and ethyl acetate. This procedure was monitored by TLC analysis. The resveratrol-rich fraction was collected to obtain a resveratrol crude product containing 50 wt % of resveratrol. The crude product was recrystallizated with ethanol to obtain 3.1 g of resveratrol crystal, the second extract of lingonberry containing 65 wt % of resveratrol. FIG. 2 shows its HPLC spectrum, using chromatographic Condition 3 as described above.

Example 10

Preparation of a Second Extract of Lingonberry

The fruit raw material (200 g), which had been extracted as described in Example 2, was further extracted with n-hexane under a light-proof and nitrogen gas atmosphere. The extract solution was transferred into a silica gel column directly, washed with n-hexane to remove impurities, and then gradiently eluted with a mixture of n-hexane and ethyl acetate. This procedure was monitored by TLC analysis. The resveratrol-rich fraction was collected to obtain a resveratrol crude product containing 70 wt % of resveratrol. The crude product was recrystallizated with ethanol to obtain 2.0 g of resveratrol crystal, the second extract of lingonberry containing 80 wt % of resveratrol.

Example 11

Preparation of a Third Extract of Lingonberry

Figure 3:
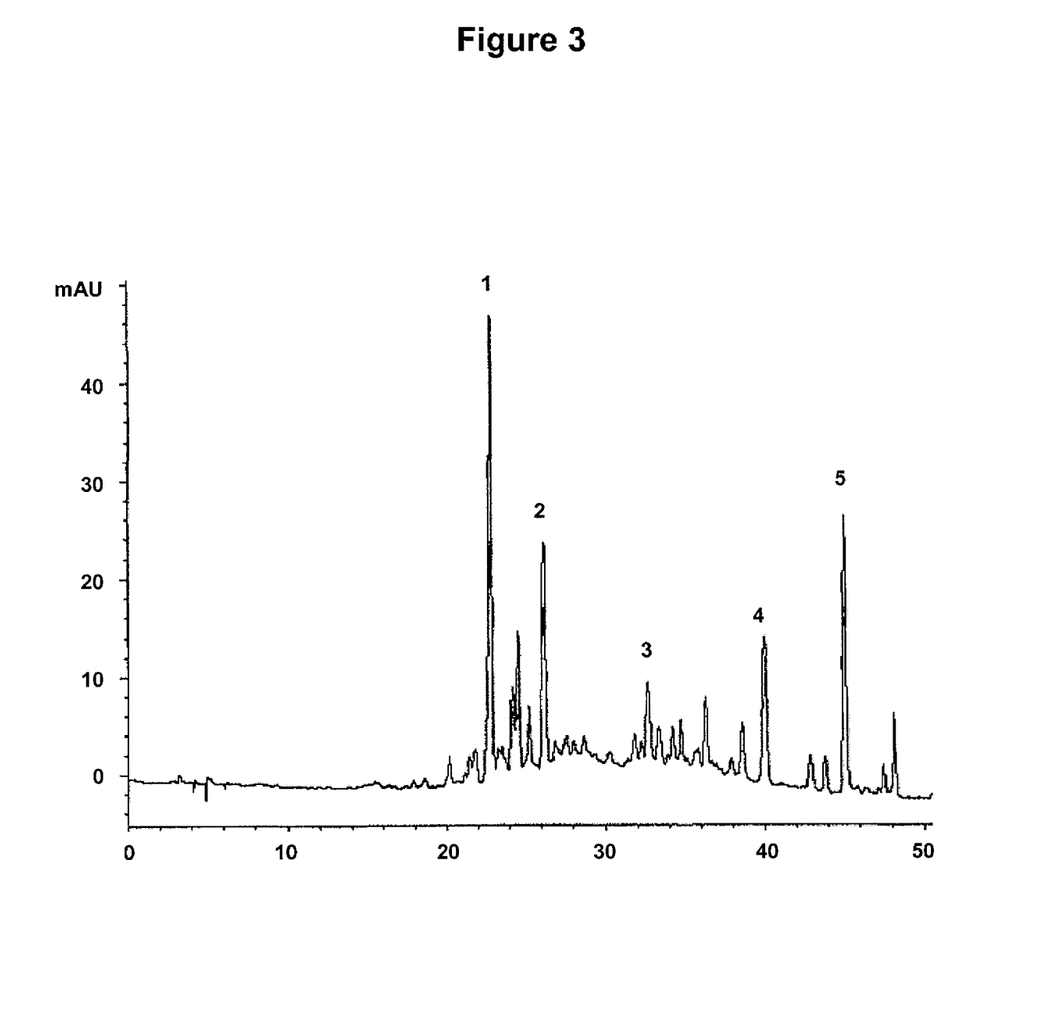
FIG. 3 is a HPLC spectrum of a third extract obtained as provided herein. Peak 1=anthocyan, peaks 2-4=pro cyanidin, and peak 5=resveratrol.

The first extract described in Example 3 (0.89 g, containing 24.5 wt % of anthocyanin, 67.7 wt % of proanthocyanin, and 1.5 wt % of resveratrol) and the second extract of Example 10 (0.11 g, containing 80 wt % of resveratrol) were mixed, dissolved in ethanol, vacuum-concentrated, and spray-dried to obtain 1.00 g of a third extract, which contained 21.8 wt % of anthocyanin, 60.2 wt % of proanthocyanin and 10.0 wt % of resveratrol. FIG. 3 shows the HPLC spectrum of the third extract in this example using chromatographic Condition 2 as described above.

Example 12

In Vitro Anti-oxidation of a First Extract of Lingonberry

The first extract of lingonberry from Example 7, containing 5.2 wt % of anthocyanin, 22.3 wt % of proanthocyanin, and 0.5 wt % of resveratrol, was dissolved in double-distilled water and diluted into solutions in serial concentrations of 0.5, 0.25, 0.125, 0.0625, 0.03125, 0.015625, and 0.0078125 mg/ml. Ascorbic acid was likewise diluted to serial concentrations of 2, 1, 0.5, 0.25, 0.125, and 0.0625 mg/ml. The anti-oxidation effect of lingonberry extracts was confirmed by determining the hydroxyl radical (.OH) and the scavenging effect of the test drug on the hydroxy radical using the orthophenanthroline $Fe^{2+}$ oxidation method.

The total reaction volume was 4.7 ml, and thus the final concentrations of ascorbic acid solution were 0.851, 0.426, 0.213, and 0.106 mg/ml, while the final concentrations of lingonberry extract were 0.106, 0.053, 0.027, 0.013 mg/ml. Measurements were obtained for five samples in each group, and the scavenging rates of .OH were calculated and averaged. In order to verify the reliability of this method, ascorbic acid, a known .OH scavenging agent was used as a positive control when evaluating the scavenging effect of the lingonberry extract on hydroxy radicals during the experiment. The $IC_{50}$ for ascorbic acid was 0.3078 mg/ml. The $IC_{50}$ for the extract of lingonberry was 0.1181 mg/ml. The results of these experiments are shown in Tables 1 and 2.

TABLE 1

Scavenging effects of ascorbic acid on hydroxy radical (n = 4)

| Final concentration (mg/ml) | •OH scavenging rate (d) |
|---|---|
| 0.851 | 91.92 ± 0.77 |
| 0.426 | 40.49 ± 1.33 |
| 0.213 | 25.55 ± 2.10 |
| 0.106 | 24.44 ± 2.32 |

TABLE 2

Scavenging effect of a first extract of lingonberry
on hydroxy radical (n = 4)

| Final concentration (mg/ml) | •OH scavenging rate (d) |
|---|---|
| 0.106 | 57.30 ± 0.77 |
| 0.053 | 25.00 ± 4.65 |
| 0.027 | 23.56 ± 1.66 |
| 0.013 | 19.91 ± 3.98 |

In the reaction system of these experiments, the aqueous solution of lingonberry extract could bind with hydroxy radicals generated in the Fenton reaction, thus reducing oxidation of $Fe^{2+}$ by hydroxy radicals. Its effect on scavenging hydroxy radicals was evaluated by determining the absorbance value of the reaction system.

The extract of lingonberry may bind hydroxy radicals, reduce oxidation of $Fe^{2+}$ by hydroxy radicals and increase the concentration of orthophenanthroline-$Fe^{2+}$ conjugates in the reaction system, thereby exerting the scavenging effect on hydroxyl radicals. The scavenging capability had a dose-effect relationship with the drug concentration, in that the scavenging rate had an obviously positive correlation with concentration. The $IC_{50}$ for the extract was 0.1181 mg/ml, whereas the $IC_{50}$ for ascorbic acid (Vc) was 0.3078 mg/ml under the same experimental conditions. Consequently, the hydroxyl radical scavenging capability of the lingonberry extract was stronger than that of ascorbic acid.

Example 13

Influence of Lingonberry Extract on MDA Content and GSH-Px Activity in Mouse Blood 60 ten-month-old mice (*Mus musculus* KM), after one week's adaptable breeding, were randomly divided into 4 groups: one control group and three test groups (high, middle, and low doses of lingonberry extract). The high, middle and low dose groups were treated orally with 200, 100, and 50 mg/kg body weight of the extract of lingonberry prepared according to Example 7, which contained 5.2 wt % of anthocyanin, 22.3 wt % of proanthocyanin, and 0.5 wt % of resveratrol, and the control group was treated with distilled water at the same volume. Mice were killed after 8 weeks to determine the levels of lipid peroxide degradation product (MDA) and glutathione peroxidase (GSH-Px) in serum. The results showed that the extract of lingonberry remarkably decreased MDA content in old mice, and also increased the activity of GSH-Px in serum of old mice. Results are shown in Table 3.

TABLE 3

Influence of lingonberry extract on MDA
content and GSH-Px activity

| | MDA (nmol/ml) | GSH-Px (U/g) |
|---|---|---|
| Control group | 6.32 ± 1.12 | 59.48 ± 4.41 |
| Low Dose Group | 6.12 ± 0.91 | 69.52 ± 6.23 |
| Middle Dose Group | 5.42 ± 0.89* | 75.48 ± 6.27* |
| High Dose Group | 5.12 ± 0.94* | 83.37 ± 7.28* |

*compared with control group, P < 0.05

Example 14

Influence of Lingonberry Extract on Nutritional Obese Rats

Fifty SD male rats weighing 150-200 g were randomly divided into 5 groups according to body weight after adaptable breeding with normal feed for one week: a normal feed group, a high fat feed group, and three test groups (high dose group, middle dose group and low dose group). The normal feed group was fed with common feed, while the other groups were fed with high fat feed (55 wt % common feed, 12 wt % lard, 5 wt % sucrose, 8 wt % milk powder, 5 wt % peanut, 10 wt % eggs, 3 wt % sesame oil, and 2 wt % salt). The high, middle and low dose groups were treated with 200, 100, and 50 mg/kg body weight, respectively, of the extract of lingonberry prepared according to Example 7, containing 5.2 wt % of anthocyanin, 22.3 wt % of proanthocyanin, and 0.5 wt % of resveratrol), while the control groups were treated with distilled water at the same volume. Body weight and food-intake of the test animals were recorded each day. The animals were killed after 8 weeks, and the weights of the adipose tissue around their kidneys and testes were recorded.

In the course of the experiment, all rats grew well, presenting normal food consumption and normal behaviors. The changes in body weight, fat content, and body fat ratio (the ratio of fat around kidney and testis to body weight) of each group before and after the experiment are listed in Table 4.

TABLE 4

Influence of lingonberry extract on body weight and fat content of nutritional obese rats

| Group | | Body weight (g) | | Fat content around kidney and testes (g) | Body fat ratio |
|---|---|---|---|---|---|
| | | Before experiment | After 8 week feeding | | |
| Control groups | Normal feed | 185.30 ± 8.51 | 408.40 ± 25.98* | 10.09 ± 3.99 | 2.30 ± 0.88* |
| | High fat feed | 187.20 ± 7.93 | 465.10 ± 46.98 | 17.77 ± 7.32 | 3.14 ± 1.15 |
| Treatment dose | High dose | 186.33 ± 8.10 | 428.36 ± 41.10* | 8.92 ± 2.72* | 2.12 ± 0.56* |
| | Middle dose | 188.42 ± 6.67 | 448.33 ± 46.54* | 11.92 ± 3.19* | 2.62 ± 0.72* |
| | Low dose | 183.56 ± 7.89 | 431.73 ± 30.21* | 11.70 ± 3.45* | 2.58 ± 0.70* |

*compared with high fat feed control group, P < 0.05

It was observed that the extract of lingonberry remarkably inhibited overnutrition-induced weight gain, and decreased body fat ratio as well as the amount of fat around tissues. The extract had no influence on food consumption by the test animals. These experiments indicate that lingonberry extract can be used as health food for anti-obesity.

Example 15

Influence of Lingonberry Extract on Sod Activity and Hydroxyproline (Hyp) Content in a Photoaging Mouse Model Fifty mice (*Mus musculus* KM) weighing 15-20 g were randomly divided into 5 groups: normal control group, model control group, and 3 test groups including high, middle and low dose groups. Mice in each group except the normal control group were shaved to remove back hair, and then were irradiated with a UVA lamp every day as a model of photoaging. The high, middle and low dose groups were treated orally with 200, 100, and 50 mg/kg body weight of the extract of lingonberry prepared according to Example 7, containing 5.2 wt % of anthocyanin, 22.3 wt % of proanthocyanin, and 0.5 wt % of resveratrol, while the control groups were treated with distilled water at the same volume. After 8 weeks, the mice were killed and skin was immediately removed from the shaved area. Skin samples were tested for local SOD activity and HYP content using biochemical methods. The results are shown in Table 5.

TABLE 5

Influence of lingonberry extract on SOD activity and HYP content in a photoaging mouse model

| | SOD (NU/mg prot) | HYP (nmol/mg prot) |
|---|---|---|
| Normal control group | 43.15 ± 7.21* | 2.85 ± 0.69* |
| Model control group | 12.99 ± 2.16 | 1.11 ± 0.24 |
| High dose group | 22.63 ± 3.74* | 2.68 ± 0.65* |
| Middle dose group | 17.85 ± 4.33 | 1.82 ± 0.39 |
| Low dose group | 16.38 ± 4.38 | 1.56 ± 0.50 |

*compared with model control group, $P < 0.05$

It was observed that the extract of lingonberry could inhibit skin aging, as it increased SOD activity and HYP content in the skin of treated mice. Such effects would be expected to keep skin energetic and elastic, suggesting that lingonberry extracts are useful in health foods and cosmetics.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising:
a first extract of lingonberry fruit, said first extract comprised of 5-20 wt % of anthocyanin, 50-95 wt % of proanthocyanin, less than 2 wt % of resveratrol, and the balance of other components, and
a second extract of lingonberry fruit, said second extract comprising 60-98 wt % of resveratrol, wherein said first extract of lingonberry fruit is obtained by:
(a) extracting lingonberry fruit with a first solvent, said first solvent being an aqueous acid solution or an aqueous acid-alcohol solution containing no more than 10 wt % of hydrochloric acid, sulfuric acid, acetic acid or citric acid, or an aqueous solution containing 0.05-0.2 wt % of cellulase or pectinase;
(b) evaporating said first extract solution to obtain a crude first extract; and
(c) purifying said crude first extract to obtain a said first extract, wherein said purifying comprises:
transferring said crude first extract into an absorptive resin column or an ion exchange resin column, eluting with 30-95% ethanol, concentrating the obtained eluate, and drying; or
passing said crude first extract through an ultrafiltration membrane, concentrating the obtained retentate or passing the retentate over a reverse osmosis membrane, and drying the obtained concentrated solution; or
combining the above two methods by passing said crude first extract through an ultrafiltration membrane, purifying the obtained retentate with a resin column, and drying; or
passing the crude first extract over a resin column, then treating with an ultrafiltration membrane, and drying, to form said first extract;
and wherein said second extract of lingonberry fruit is obtained by steps of:
(d) re-extracting the extracted lingonberry fruit of step (a) with a second solvent to obtain a second extract solution, wherein said second solvent is ethyl acetate, benzene, toluene, chloroform, dichloromethane, n-hexane, acetone, methanol, ethanol, or a mixture thereof, or 70-95 wt % methanol or ethanol aqueous solution, or an enzyme aqueous solution containing 0.01-0.3 wt % of cellulase or pectase;
(e) concentrating said second extract solution to obtain a crude second extract; and
(f) purifying said crude second extract using silica gel column chromatography with n-hexane, ethyl acetate, acetone, chloroform, dichlormethane, methanol, ethanol, or a mixture thereof as the eluent,
to form said second extract, and wherein said first extract and said second extract are combined to form said composition.

* * * * *